United States Patent [19]

Sarashina

[11] 4,413,994
[45] Nov. 8, 1983

[54] INTESTINAL IRRIGATOR FOR USE WITH ARTIFICIAL ANUS

[75] Inventor: Hiromi Sarashina, Sakura, Japan

[73] Assignee: Senko Medical Instrument Mfg. Co., Ltd., Tokyo, Japan

[21] Appl. No.: 357,741

[22] Filed: Mar. 12, 1982

[30] Foreign Application Priority Data

Mar. 18, 1981 [JP] Japan .............................. 56-38004[U]

[51] Int. Cl.³ ................................................ A61F 5/44
[52] U.S. Cl. .................................................... 604/327
[58] Field of Search ............... 604/332, 327, 333, 334, 604/335, 338, 339, 341, 342, 19, 28

[56] References Cited

U.S. PATENT DOCUMENTS

| | | | |
|---|---|---|---|
| 2,154,202 | 4/1939 | Gricks | 604/343 |
| 3,608,540 | 9/1971 | Sartorius | 604/28 |
| 3,718,141 | 2/1973 | Goetz | 604/333 |
| 3,896,810 | 7/1975 | Akiyama | 604/272 |

Primary Examiner—John D. Yasko
Attorney, Agent, or Firm—Darby & Darby

[57] ABSTRACT

An intestinal irrigator adapted for use with an artificial anus which includes a body having a hollow portion having open front and rear ends. The hollow portion has a bag-mounting portion. A suction portion is arranged around the hollow portion. The suction portion has an open front end which lies flush with the open front end of the hollow portion. The suction portion has a suction port connectable to a suction source. A liquid supply portion is connected to the hollow portion and is connectable to a liquid supply source for supplying a liquid to the interior of the hollow portion.

5 Claims, 4 Drawing Figures

INTESTINAL IRRIGATOR FOR USE WITH ARTIFICIAL ANUS

BACKGROUND OF THE INVENTION

1. Field of the Invention

This invention relates to an intestinal irrigator for use with an artificial anus.

2. Prior Art

In recent years, quite a few patients suffereing from cancer of the rectum have been subjected to a surgical operation to remove the rectum and implant an artifical anus in the body. The patients having such an implanted artificial anus must undergo an intestinal irrigating treatment periodically. In this intestinal irrigating treatment, an irrigating liquid such as warm water is supplied into the intestines through the artificial anus and then is discharged therefrom.

One conventional intestinal irrigator is shown in FIG. 1. The intestinal irrigator 100 includes a body which comprises an outer cylindrical wall 101 having a front end 101a, the rear end of the outer cylindrical wall 101 being closed by a circular end wall 102. An inner cylindrical wall 103 is disposed within the outer cylindrical wall 101 in coaxial relation thereto and extends from the end wall 102. The inner cylindrical wall 103 has a front end 103a which lies flush with the front end 101a of the outer cylindrical wall 101. With this construction, an annular chamber 105 is defined by the outer and inner cylindrical walls 101 and 103 and a marginal portion 106 of the end wall 102 lying between the two cylindrical walls 101 and 103, the annular chamber serving as a suction chamber. A tubular portion 108 is formed on the outer surface of the outer cylindrical wall 103 and is in communication with the annular suction chamber 105. A circular aperture 109 is formed through the end wall 102 at the center thereof. An irrigating tube 110 is sealingly fitted in the aperture 109 and extends into an inner chamber 111 defined by the inner cylindrical wall 103 and the end wall 102, a forward end 110a of the irrigating tube 110 projecting beyond the front ends 101a and 103a of the outer and inner cylindrical walls 101 and 103. The tubular portion 108 is connectable to a suction source through a suction tube for creating a preselected degree of negative pressure within the annular suction chamber 1, as will hereinafter more fully be described. A three-way valve may be mounted on the suction tube.

For carrying out the intestinal irrigating treatment using the intestinal irrigator 100, the forward end 110a of the irrigating tube 110 is inserted into an artificial anus implanted in a patient until the front ends 101a and 103a of the outer and inner cylindrical walls 101 and 103 are brought into contact with the belly of the patient, so that the artificial anus is disposed within the inner chamber 111. Then, the intestinal irrigator is fixed to the belly of the patient by a belt or the like. The tubular portion 108 is connected to the suction source through the suction tube so that a predetermined degree of negative pressure, for example, on the order of 100 to 150 mmHg, is created within the annular suction chamber 105. Thus, the intestinal irrigator 100 is positively retained in position by suction, and the front ends 101a and 103a of the outer and inner cylindrical walls 101 and 103 are held in sealing engagement with the belly of the patient. Then, the rear end of the irrigating tube 110 remote from its forward end 110a is connected to a source of an irrigating liquid, and the irrigating liquid is supplied through the irrigating tube 110 to the intestines of the patient. Then, the suction of the suction chamber 105 is released, and the intestinal irrigator 100 is detached from the belly of the patient with the irrigating tube 110 withdrawn from the artificial anus. Upon lapse of an appropriate length of time, an open end of a bag made of vinyl is brought into contact with the belly of the patient in surrounding relation to the artificial anus. The supplied irrigating liquid and matters in the intestines are discharged therefrom into the bag.

This conventional intestinal irrigator 100 is disadvantageous in that the artificial anus is susceptible to damage by the irrigating tube 110 since the irrigating tube 110 must be inserted into the artificial anus to carry out the intestinal irrigating treatment. This is quite dangerous.

Another disadvantage is that it is rather cumbersome to handle this conventional intestinal irrigator since the bag must be attached directly to the belly of the patient after the intestinal irrigator is detached from the belly.

A further disadvantage is that the irrigating tube, when once used, can not be adequately cleaned since it has a small diameter. Therefore, the once-used intestinal irrigator must be discarded from a sanitary point of view. That is quite undesirable from an economical viewpoint.

SUMMARY OF THE INVENTION

It is therefore an object of this invention to provide an intestinal irrigator which will not damage an artificial anus and can be easily handled and repeatedly used.

According to the present invention, there is provided an intestinal irrigator adapted for use with an artificial anus which irrigator comprises a body including a hollow portion having open front and rear ends, the hollow portion having a bag-mounting portion; a suction portion mounted around the hollow portion, the suction portion having an open front end, the open front end of the suction portion lying flush with the open front end of the hollow portion; and the suction portion having a suction port connectable to a suction source; and a liquid supply portion connected to the hollow portion, the liquid supply portion being connectable to a liquid supply source for supplying a liquid to the interior of the hollow portion.

DETAILED DESCRIPTION OF THE PREFERRED EMBODIMENTS

Figure 1:
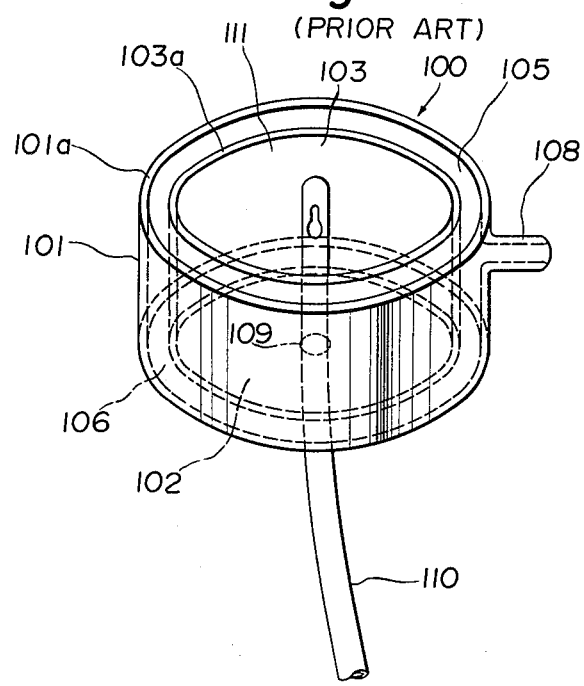
FIG. 1 is a perspective view of an intestinal irrigator provided in accordance with the prior art.
Figure 2:
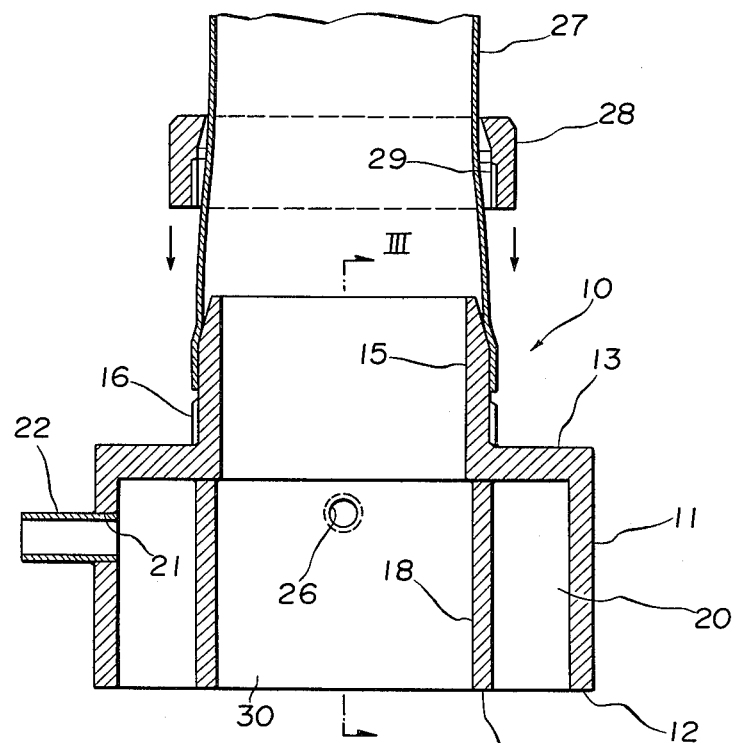
FIG. 2 is a cross-sectional view of an intestinal irrigator provided in accordance with the present invention.
Figure 3:
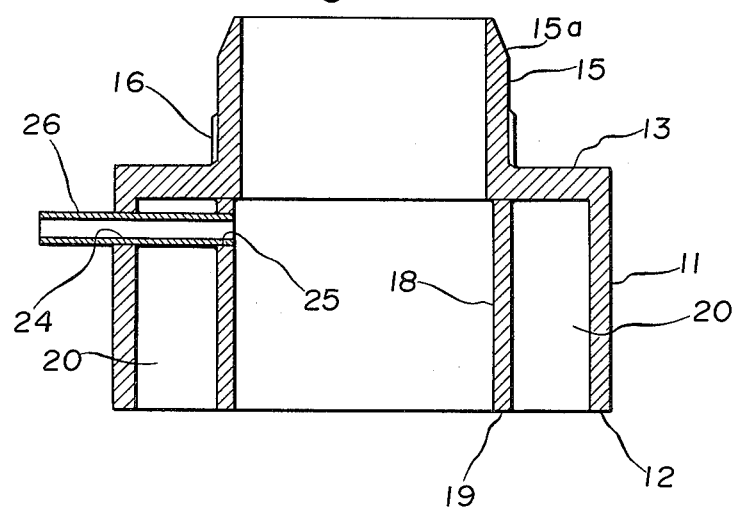
FIG. 3 is a cross-sectional view taken along the line III—III of FIG. 2.

FIGS. 2 and 3 show an intestinal irrigator 10 provided in accordance with the present invention. The intestinal irrigator 10 includes a body which comprises an outer cylindrical wall 11 having a front end 12. The outer cylindrical wall 11 has an annular wall 13 formed integrally on a rear end thereof and disposed perpendicularly to the axis of the outer cylindrical wall 11. A rear cylindrical wall 15 of a smaller diameter extends outwardly from an inner peripheral edge of the annular wall 13, the rear cylindrical wall 15 being disposed in coaxial relation to the outer cylindrical wall 11. The rear cylindrical wall 15 has an externally-threaded section 16 formed on its outer circumferential surface adjacent to the annular wall 13. The outer circumferential surface of the rear cylindrical wall 15 is tapered at its free end portion 15a. The rear cylindrical wall 15 serves as a bag-mounting portion as will hereinafter more fully be described.

An inner cylindrical wall 18 extends from the annular wall 13 in a direction away from the rear cylindrical wall 15, the inner cylindrical wall 18 being disposed in coaxial relation to the outer cylindrical wall 11 and the rear cylindrical wall 15. The inner cylindrical wall 18 is slightly larger in diameter than the rear cylindrical wall 15. A front end 19 of the inner cylindrical wall 18 lies flush with the front end 12 of the outer cylindrical wall 11.

An annular suction chamber 20 is defined by the outer and inner cylindrical walls 11 and 18 and the annular wall 13. The outer cylindrical wall 11 has an aperture 21 formed therethrough, and a tubular fitting 22 is hermetically fitted into the aperture 21.

A pair of aligned apertures 24 and 25 are formed respectively through the outer and inner cylindrical walls 11 and 18. A second tubular fitting 26 extends through the aperture 24 and the annular suction chamber 20 into the aperture 25, the fitting 26 being hermetically fitted in the apertures 24 and 25.

A bag 27 made, for example, of vinyl is adapted to be fitted on the rear cylindrical wall 15 at its one end. A retaining ring 28 is adapted to be fitted on the rear cylindrical wall 15 with the one end of the bag being interposed therebetween. The retaining ring 28 has an internally-threaded section 29 which are adapted to be screwed onto the externally-threaded section 16 of the rear cylindrical wall 15 to hold the bag 27 against movement relative thereto. Since the rear cylindrical wall 15 has the tapered end 15a as described above, the attachment of the bag 27 to the rear cylindrical wall 15 is facilitated.

For carrying out an intestinal irrigating treatment using the intestinal irrigator 10, the front ends 12 and 19 of the outer and inner cylindrical walls 11 and 18 are brought into contact with the belly of a patient having an implanted artificial anus, the artificial anus being disposed within the inner cylindrical wall 18. Then, the intestinal irrigator 10 is fixed to the belly of the patient by a belt or the like. Then, the fitting 22 is connected through a tube with a three-way valve to a suction source such as a vacuum pump, so that a preselected degree of negative pressure is created within the annular suction chamber 20 to positively retain the intestinal irrigator 10 in position by suction. In this condition, the front ends 12 and 19 of the outer and inner cylindrical walls 11 and 18 are held in sealing engagement with the belly of the patient. Then, the bag 27 having a length of about 1 m is fitted on the rear cylindrical wall 15 at one end thereof. The retaining ring 28 is fitted on the rear cylindrical wall 15 with the internally-threaded section 29 screwed onto the externally-threaded section 16 of the rear cylindrical wall 15. The one end of the bag 27 is interposed between the rear cylindrical wall 15 and the retaining ring 28 and held against the rear cylindrical wall 15 in a liquid tight manner. The bag 27, which is also open at the other end, is clamped or tied intermediate the opposite ends thereof by a suitable clamping member in a liquid tight manner. Then, the fitting 26 is connected through a liquid supply tube to a liquid source in the form of a container holding an irrigating liquid such as warm water. The container is held at a level above the artificial anus so that the irrigating liquid is supplied by gravity to the inner chamber 30 defined by the inner cylindrical wall 18. A clamp member is adapted to be detachably attached to the liquid supply tube to control the flow of the irrigating liquid therethrough. Then, the irrigating liquid is supplied from the container to the inner chamber 30 under the influence of gravity, the irrigating liquid being introduced through the artificial anus into the intestines of the patient. The amount of the irrigating liquid introduced into the intestines is 1 to 5 liters. The irrigating liquid is retained in the intestines for a while. During this time, the suction of the suction chamber 20 may be released. Then, the free end of the bag 27 is placed in a suitable receptacle such as a toilet stool, and the clamping member, clamping the bag 27 intermediate its opposite ends, is loosened. Thereafter, the irrigating liquid retained in the intestines and the matters therein are discharged into the receptacle. Thus, the intestinal irrigating treatment is completed. Then, the suction of the suction chamber 20 is released, and the intestinal irrigator 10 is detached from the belly of the patient by removing the belt. The retaining ring 28 is removed from the rear cylindrical wall 15 to detach the bag 27 therefrom. The used bag 27 is discarded. The intestinal irrigator 10 is washed for reuse.

Figure 4:
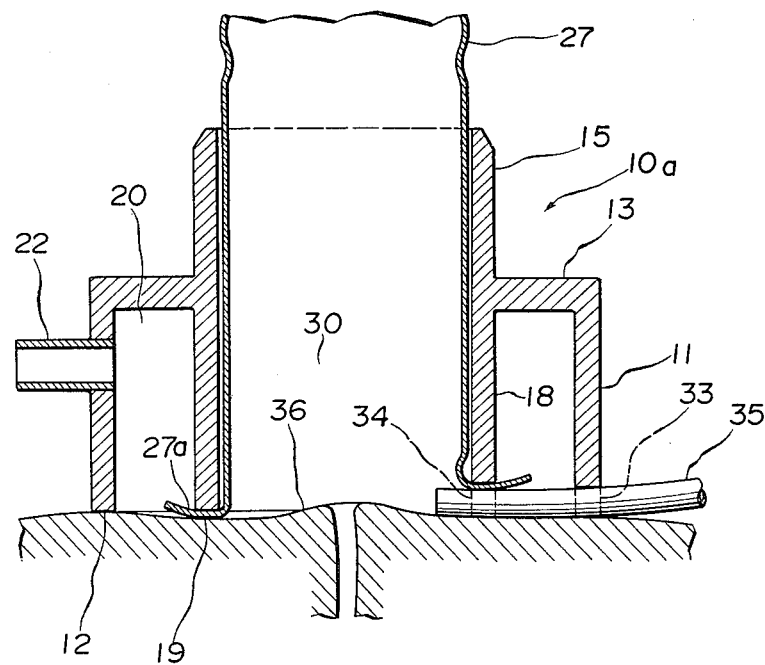
FIG. 4 is a cross-sectional view of a modified intestinal irrigator.

FIG. 4 shows a modified intestinal irrigator 10a. The intestinal irrigator 10a is substantially similar in construction to the intestinal irrigator 10 in the proceding embodiment in FIGS. 2 and 3. The irrigator 10a differs from the irrigator 10 in that it is not provided with the apertures 24 and 25 and the second tubular fitting 26. Instead, a pair of aligned notches 33 and 34 are formed respectively in the front ends 12 and 19 of the outer and inner cylindrical walls 11 and 18. A liquid supply tube 36 made of a resilient material is adapted to be tightly fitted in these aligned notches 33 and 34. The bag 27 is adapted to be received in the rear and inner cylindrical walls 15 and 18 with its inner end 27a turned outwardly at the front end 19 of the inner cylindrical wall 18.

For carrying out an intestinal irrigating treatment using the intestinal irrigator 10a, the bag 27 is inserted into the rear and inner cylindrical walls 15 and 18 with its inner end 27a turned outwardly at the front end 19 of the inner cylindrical wall 18. Then, the liquid supply tube 35 is fitted in the notch 33 and is further fitted in the notch 34 with the inner end 27a of the bag 27 firmly clamped between the notch 34 and the liquid supply tube 34. Then, the intestinal irrigator 10a is attached to the belly 36 of the patient by the suction of the suction chamber 20, as described above for the intestinal irrigator 10. In this condition, the inner end 27a of the bag 27 is sealingly held between the front end 19 of the inner cylindrical wall and the belly 36. Thus, in this embodiment, the front end 19 serves as a bag retaining means. The liquid supply tube 35 is sealingly fitted in the aligned notches 33 and 34 due to the resilient properties thereof. Also, the liquid supply tube 35 is sealingly held against the belly 36. Therefore, the irrigating liquid within the inner chamber 30 of the inner cylindrical wall 18 is prevented from leaking through the notch 34. Also, the ambient air will not intrude into the suction chamber 20 through the notch 33. Then, the irrigating liquid is supplied from the liquid source to the inner chamber 30, and the intestinal irrigating treatment is conducted as described above for the intestinal irrigator 10. With this construction, only the bag 27 is contaminated by the matters discharged from the intestines of the patient. Therefore, a cleaning operation of the intestinal irrigator 10a is much facilitated.

In the above two embodiments, the annular suction chamber 20 may be replaced by a plurality of suction cups mounted around the inner cylindrical wall 18, the open end of each suction cup lying flush with the front end 19 of the inner cylindrical wall 18. The suction cups are connected to the suction source.

The intestinal irrigator 10a may not be provided with the rear cylindrical wall 15.

As described above, the intestinal irrigators 10 and 10a are of such a construction that no part thereof make mechanical contact with the artificial anus, thereby preventing it from being damaged. Further, these intestinal irrigators can be easily handled and used repeatedly.

What is claimed is:

1. An intestinal irrigator adapted for use with an artificial anus which irrigator comprises:
   (a) a body including a hollow portion having open front and rear ends, said hollow portion having a bag-mounting portion;
   (b) a suction portion mounted around said hollow portion, said suction portion having an open front end, said open front end of said suction portion lying flush with said open front end of said hollow portion; and said suction portion having a suction port connectable to a suction source; and
   (c) a liquid supply portion connected to said hollow portion, said liquid supply portion being connectable to a liquid supply source for supplying a liquid to the interior of said hollow portion.

2. An intestinal irrigator according to claim 1, in which said hollow portion comprises a cylindrical wall, said body comprising an outer cylindrical wall disposed in coaxial and spaced relation to said hollow portion, said body comprising an annular wall extending between the rear ends of said hollow portion and said outer cylindrical wall, and said hollow portion, said outer cylindrical wall and said annular wall defining an annular chamber serving as said suction portion.

3. An intestinal irrigator according to claim 2, in which said body further comprises a rear cylindrical wall extending from the rear end of said hollow portion in coaxial relation thereto, said rear cylindrical wall serving as said bag mounting portion, and a retaining ring being adapted to fit on said rear cylindrical wall.

4. An intestinal irrigator according to claim 2, in which said liquid supply portion comprises a fitting extending hermetically through said outer cylindrical wall and said hollow portion.

5. An intestinal irrigator according to claim 2, in which a pair of aligned notches are formed respectively in the front ends of said outer cylindrical wall and hollow portion, said liquid supply portion comprising a resilient tube sealingly fitted in said aligned notches.

* * * * *